United States Patent
Regensburger et al.

(10) Patent No.: US 11,389,122 B2
(45) Date of Patent: Jul. 19, 2022

(54) METHOD FOR REGISTERING AN X-RAY IMAGE DATA SET WITH A NAVIGATION SYSTEM, COMPUTER PROGRAM PRODUCT, AND SYSTEM

(71) Applicant: Siemens Healthcare GmbH, Erlangen (DE)

(72) Inventors: Alois Regensburger, Erlangen (DE); Oliver Hornung, Dormitz (DE); Martin Ostermeier, Buckenhof (DE)

(73) Assignee: Siemens Healthcare GmbH, Erlangen (DE)

( * ) Notice: Subject to any disclaimer, the term of this patent is extended or adjusted under 35 U.S.C. 154(b) by 119 days.

(21) Appl. No.: 17/019,697

(22) Filed: Sep. 14, 2020

(65) Prior Publication Data

US 2021/0085266 A1    Mar. 25, 2021

(30) Foreign Application Priority Data

Sep. 19, 2019  (DE) .......................... 102019214302.4

(51) Int. Cl.
  *G06T 7/00*  (2017.01)
  *A61B 6/04*  (2006.01)
  *A61B 6/00*  (2006.01)

(52) U.S. Cl.
  CPC .......... *A61B 6/0492* (2013.01); *G06T 7/0012* (2013.01); *A61B 6/585* (2013.01);
  (Continued)

(58) Field of Classification Search
  CPC ....... A61B 6/0492; A61B 6/585; A61B 6/032; A61B 34/20; A61B 90/37; A61B 8/0841; G06T 7/0012
  See application file for complete search history.

(56) References Cited

U.S. PATENT DOCUMENTS

| 2013/0066196 A1 | 3/2013 | Graumann |
| 2014/0051994 A1 | 2/2014 | Graumann |
| 2016/0191887 A1* | 6/2016 | Casas .................... G06T 19/006 348/47 |

FOREIGN PATENT DOCUMENTS

| DE | 102010020781 A1 | 11/2011 |
| DE | 102011007796 A1 | 10/2012 |
| WO | 2010145975 A1 | 12/2010 |

OTHER PUBLICATIONS

German Office Action for German Application No. 10 2019 214 302.4 dated Jul. 13, 2020.

* cited by examiner

*Primary Examiner* — Don K Wong
(74) *Attorney, Agent, or Firm* — Lempia Summerfield Katz LLC

(57) ABSTRACT

The disclosure relates to methods, systems, and computer program products for registering a set of X-ray images with a navigation system. In the method, by a camera, at least one image of a reference object is recorded and, on the basis thereof, a current posture of the reference object is determined. It is then checked whether this posture fulfils a specified criterion, which also on an arrangement of the reference object at least partially outside a planned reconstruction volume of the X-ray device, predicts an expected successful registration. On non-fulfillment of the criterion, a signal for adaptation of a relative alignment between the X-ray device and the reference object is automatically output. On fulfillment of the criterion, the X-ray images of the reference object are recorded, the posture of the reference object is determined, and the registration is carried out using the determined postures as reference.

15 Claims, 2 Drawing Sheets

(52) U.S. Cl.
CPC ............... *G06T 2207/10116* (2013.01); *G06T 2207/30008* (2013.01); *G06T 2207/30024* (2013.01); *G06T 2207/30056* (2013.01)

METHOD FOR REGISTERING AN X-RAY IMAGE DATA SET WITH A NAVIGATION SYSTEM, COMPUTER PROGRAM PRODUCT, AND SYSTEM

The present patent document claims the benefit of German Patent Application No. 10 2019 214 302.4, filed Sep. 19, 2019, which is hereby incorporated by reference.

TECHNICAL FIELD

The disclosure relates to a method for registering a set of X-ray images recorded or to be recorded by an X-ray device with a navigation system, a corresponding computer program product, and a system for carrying out the method.

BACKGROUND

In technology-based medicine or computer-assisted surgery (CAS), navigated applications or methods are known in which, for example, an instrument may be navigated along a planned path to a specified region of interest. For methods of this type, X-ray images may be registered with the respective navigation or tracking system, in order to provide an accurate and reliable navigation function. For this purpose, for example, an X-ray visible marker is positioned in a reconstruction volume of the X-ray device, that is, in a spatial region which is recorded or mapped in all the 2D projection images recorded by the X-ray device and then therefrom may be reconstructed three-dimensionally, and are simultaneously positioned in the acquisition region of the navigation system.

However, it has previously been difficult to ensure in advance that the marker is actually situated in the reconstruction volume or the corresponding spatial region. Conventionally, the respective physician or radiographer estimates by eye whether the marker is correctly positioned for an expected successful registration before the relevant X-ray projection images are recorded. This may lead to the registration of the X-ray device to the navigation system after the recording of the projection images failing or having an excessively large error, that is, an excessively large inaccuracy. There already exists the approach of initially recording only, for example, two projection images in a lateral projection and AP projection and of checking whether the marker is visible in these two projection images. However, this already represents a significant additional expenditure of time and effort and an additional radiation burden for the respective patient. Merely the fact that the marker is visible in these two editorial images is also unable to guarantee reliably that the marker will actually lie completely within the planned reconstruction volume.

In the event of a failed registration, the marker may possibly be positioned anew and a further registration attempt including renewed recording of projection images may be carried out or the respective intervention or procedure may be carried out without navigation. Neither of these two possibilities represents a satisfactory solution from a present-day viewpoint.

SUMMARY AND DESCRIPTION

It is an object of the present disclosure to enable a more robust registration possibility for X-ray devices and navigation systems. The scope of the present disclosure is defined solely by the appended claims and is not affected to any degree by the statements within this summary. The present embodiments may obviate one or more of the drawbacks or limitations in the related art.

A method serves to register a set of X-ray images recorded or to be recorded by an X-ray device (and thus also to register the X-ray device) with a navigation system. The registering of these images or devices with or to one another may include a registering of their respective coordinate systems used internally by the devices or for data recorded or generated with the devices or of these coordinate systems with a specified third or common coordinate system.

The X-ray device may be a C-arm X-ray device. Other types of X-ray device may also be used. The X-ray device may enable only a relative movement between, firstly, the X-ray source and the detector of the X-ray device and, secondly, an examination object imaged thereby or a corresponding spatial volume.

The navigation system may be an optical navigation system which may have one or more cameras, (e.g., optical cameras), for capturing and tracking objects in the recording region (FoV, field of view) or the reconstruction volume of the X-ray device. Similarly, other types of navigation systems, (e.g., for electromagnetic navigation or tracking of objects), may be used.

In a method act, at least one image of a specified X-ray visible reference object arranged in a recording region of the X-ray device is recorded by a camera, e.g., an optical camera. The recording region of the X-ray device in the context of the present disclosure is that spatial region which may be captured or mapped by the X-ray device in at least one position or posture of the X-ray device, (e.g., in at least one 2D projection image of a plurality of such projection images recorded for a 3D-CT data set). This is to be seen in contrast to the respective reconstruction volume which represents or includes that spatial region which, during recording of a CT data set, in particular, a cone-beam CT data set, or raw data or individual images provided for reconstruction of such a data set, (e.g., a series of many individual 2D projection images in (at least substantially) all these 2D projection images or raw data), is captured or imaged and for which a subsequent 3D reconstruction is therefore possible. The recording region may thus be regarded as a maximum field of view (FoV) and the respective reconstruction volume may be regarded as an overlap region of all the individual images or individual recordings of a recording series or image series or of an image data set in the respective application case. Accordingly, the reconstruction volume may be smaller than the recording region and may vary from application case to application case, depending upon how the X-ray device is moved or displaced for recording the respective series of 2D projection images, that is, the respective CT data set. It may therefore be possible in practice without problems and easily also to arrange the reference object reliably manually entirely within the recording region, whereas a manual positioning of the reference object in the reconstruction volume is not easily and reliably possible.

The camera may be part of the navigation system or an additional camera separate therefrom. Similarly, the camera may be part of a portable apparatus, which when performing the method is or may be carried by a respective operating person. Such a portable apparatus may be an HMD (head-mounted display), a pair of AR (augmented reality) goggles, or a pair of VR (virtual reality) goggles. In every case, the camera may be arranged in a specified or known, in particular, constant and/or monitored spatial positional relationship to the navigation system.

The reference object may be a technical object. In certain examples, the reference object may be configured asymmetrically, so that the reference object's position or orientation is determinable from different viewing directions. For this purpose, the reference object may have an arrangement of a plurality of X-ray visible reflector spheres of, for example, different sizes and/or arranged at different spacings from one another, one or more markers, a pattern, or a marking and/or the like.

Herein, at least one individual image or a plurality of images of the reference object may be recorded, wherein, this may involve a 2D image and/or a stereoscopic or 3D image in each case. If a plurality of images are recorded, they may be recorded from different directions or viewing angles, provided the camera is movably mounted.

In a further method act, a current posture, (e.g., a position and alignment or orientation of the reference object), is determined based on the at least one image recorded by the camera, in particular, automatically. This current posture may thus be determined in the coordinate system of the camera or the navigation system. Therein, a restricted accuracy, (e.g., a posture determination with an accuracy or tolerance of up to a few centimeters), may be taken into account. Herein, therefore, a rough or preliminary capture or a preliminary posture determination of the reference object is initially carried out. Accordingly, the posture determined based on the at least one camera image may also be designated a preliminary, inexact, approximately determined, or estimated posture. Because the at least one image recorded by the camera, hereinafter referred to as the camera image, is used herein, there is advantageously no significant expenditure of time or effort associated therewith and no restriction of a workflow, for example, in the context of a preparation of the respective intervention. For example, no radiation protection measures have to be taken, relevant personnel do not have to leave a region of the X-ray device and no particular recording sequence or angular position of the X-ray device has to be set.

At least a part of the X-ray device may also be captured or mapped in the at least one image by the camera or the navigation system. Based on the at least one image, accordingly, a coarse or preliminary registration of the position of the X-ray device and the navigation system may be carried out. However, this is or may also be inexact, although it is advantageously particularly simple and quick to carry out.

In a further method act, it is checked, (e.g., automatically or partially automatically), whether the current posture of the reference object determined on the basis of the at least one camera image fulfils a specified criterion, (e.g., a position or imaging criterion), which also, on an arrangement of the reference object currently at least partially outside the respective planned reconstruction volume of the X-ray device, predicts an expected successful registration in each case. For this purpose, the posture determined may, if relevant, be transferred into a coordinate system of the X-ray device according to the coarse or preliminary registration. It may thus then be checked in the coordinate system of the X-ray device whether the criterion is fulfilled.

The fulfillment of the criterion may thus mean that the registration is or will become possible at all or with at least a specified probability or at least with a specified accuracy.

A non-fulfillment of the criterion, however, may mean or may be regarded as an indication that the registration may be expected to fail or only to be carried out with an accuracy below a specified accuracy threshold value.

The planned reconstruction volume may be specified, or corresponding data may be retrieved automatically, for example, by the X-ray device or by a planning computer or the like used for planning the respective intervention.

The specified criterion may define one or more spatial conditions such as a spatial region, one or more spacings of the reference object from one or more components of the X-ray device or a system comprising it, and/or it may define one or more conditions for a mapping of the reference object by the X-ray device, (e.g., a minimum number of 2D projection images in which the reference object is mapped, a minimum angular difference between different 2D projection images mapping the reference object, and/or the like). On the basis of this criterion, before the recording of X-ray images, it may thus be checked or predicted whether the registration is expected to be successful. This advantageously enables, where required, the reference object to be repositioned promptly and the registration to be carried out reliably without, or with minimum, delay and without limitations to a respective workflow.

On non-fulfillment of the specified criterion, in a further method act, a signal is automatically output for adapting a relative alignment between the X-ray device and the reference object and/or for adapting a specified trajectory of the X-ray device provided for later recording of the X-ray images of the reference object. By this adaptation, it may be achieved that under correspondingly adapted conditions, the criterion is or will be fulfilled. Such a signal may include a corresponding indication to a respective user or respective personnel regarding the non-fulfillment of the criterion. Additionally, or alternatively, the signal may include a control or data signal for automatic adaptation of a movement or recording characteristics of the X-ray device, wherein by such an adaptation, the reconstruction volume may remain unchanged. However, with such an adaptation, a greater likelihood of the success of the registration may possibly be achieved. During or after the adaptation, the criterion may again be evaluated multiple times or continuously, that is, checked for its fulfillment. For this, during or after the adaptation, at least one further camera image may be recorded in each case, on the basis of which the posture may be determined again. For evaluating or checking the criterion, the most current posture, (e.g., the most recently determined posture), of the reference object in each case may be used. In this way, advantageously, a minimal possible adaptation may be realized particularly easily and reliably. By this, it may be prevented that other parameters or sequences are unnecessarily impaired. Additionally, or alternatively, before the adaptation, a deviation that has led to the non-fulfillment of the criterion, or accordingly the necessary adaptation, (e.g., with regard to a scope or amount), a direction or a difference from the previously provided trajectory or the like may be calculated or estimated. In this way, an arrangement or situation in which the criterion is fulfilled may advantageously be achieved and set particularly rapidly. This may be the case because a corresponding calculation may be carried out, where relevant, significantly faster than, for example, an act-by-act adaptation with respective renewed checking of the criterion after each act.

On fulfillment of the specified criterion for the particular posture of the reference object and/or with the possibly adapted relative position and/or the possibly adapted trajectory, that is, for the current posture or situation, or the current posture or situation after the adaptation, in a further method act, by the X-ray device, the X-ray or projection images of the reference object are recorded, in particular, from a plurality of different viewing angles. From these X-ray images, the posture of the reference object is then determined, in particular, automatically. On the basis of the X-ray images, the posture of the reference object may possibly be determined with greater accuracy or higher resolution than on the basis of the at least one camera image. Accordingly, the posture determined on the basis of the X-ray images, also designated the exact posture or precise posture, even if in principle both cases may relate to the same posture of the reference object, the posture of the reference object has thus not changed, seen objectively, between the recording of the at least one camera image and the X-ray images.

The current posture of the reference object is thus determined here, for example, from the viewpoint of or in the coordinate system of the X-ray device. By this, or through the combination of the corresponding data, the registration of the X-ray device with the navigation system is carried out, (e.g., automatically or partially automatically), making use of the determined postures as a reference, that is, in relation to the determined postures of the reference object. Thereby, apart from the posture determined on the basis of the X-ray images, the at least one camera image previously recorded in the context of the described coarse or preliminary capture, or the posture determined therefrom, may be used. Similarly, the reference object may again be mapped or captured by the camera and/or by the navigation system and on the basis of corresponding capture data, the posture of the reference object may be determined anew from the viewpoint or in the coordinate system of the camera or the navigation system. This may be useful in order herein to determine the posture with greater accuracy, for example, in that in comparison with the coarse or preliminary capture, a plurality of camera images are recorded, and/or camera images from additional viewing angles or the reference object is additionally or alternatively captured here by the navigation system if the aforementioned camera is not part of the navigation system.

The method described may be carried out iteratively. If, therefore, on non-fulfillment of the criterion, after the signal, the reference object is repositioned or realigned (e.g., automatically or manually), then in the next iteration act or pass of the method, the criterion is carried out anew with the updated posture of the reference object. Thus, at least one new camera image may be recorded, on the basis thereof, the updated posture of the reference object determined, and the criterion checked anew for this updated posture. This iteration loop may be carried out or run through until the fulfillment of the criterion is determined.

By the present disclosure, the success of the registration may be provided in advance, (that is, before the recording of X-ray images and the actual registration calculation), particularly easily, rapidly, and reliably. Further, registration errors and corresponding delays or restrictions in the respective intervention may be prevented. Similarly, using the present disclosure, the registration may also be carried out or instigated reliably by inexperienced personnel. In addition, with significantly reduced expenditure of time and effort as compared with previous methods, a boundary region for the positioning of the reference object for a successful registration may be sought out.

By this, a more flexible positioning of the reference object is possible overall, because a larger spatial region for positioning the reference object for the registration may be used practicably. By this, for example, also in cases with restricted space conditions, a registration may be achieved with a practicable effort and thus a navigation support for the respective intervention may be enabled, for example, in cases in which a center of the recording region or of the reconstruction volume of the X-ray device is already occupied or restricted by the respective patient and/or further devices or instruments, so that the reference object cannot be positioned there for the registration. In such cases, the reference object would have to be positioned by eye for a reliable registration, for example, within the respective patient, which is not practicably possible. If the reference object is then placed, for example, from outside on the patient, it is not immediately and reliably evident, even to experienced personnel, in which positions or orientations the reference object is then situated entirely or partially within the reconstruction volume or in which positions or postures a sufficiently exact registration results by mapping in sufficiently different projection images with a sufficiently large angular offset.

In an advantageous embodiment, it is checked as the criterion or as part of the criterion whether the reference object is situated in a specified permitted spatial region. For this purpose, the permitted spatial region may be defined, for example, in the coordinate system of the camera or of the navigation system. Similarly, the permitted spatial region may be defined in the coordinate system of the X-ray device or in relation to the X-ray device, for example, if the preliminary registration has been carried out as described on the basis of the at least one camera image.

Similarly, the permitted spatial region may be defined, for example, by one or more spacings from one or more components of the X-ray device which may also be mapped in the at least one camera image. Additionally, or alternatively, the permitted spatial region may be defined by specified distance details for one or more directions or dimensions, for example, along axes of symmetry or central axes of a patient table in the field of view of the camera, starting from a specified defined point and/or the like.

Corresponding spacings may be determined, for example, on the basis of the at least one camera image, by the corresponding image processing or a corresponding image processing algorithm, for example, on the basis of an automatic or partially automatic object or feature recognition.

The permitted spatial region may be defined dependent upon an orientation of the reference object, because in a particular position of the reference object, the success of the registration may depend upon its orientation or alignment.

The permitted spatial region may be determined or defined once in advance for the respective individual X-ray device, for example, by corresponding experiments and may then advantageously be retrieved or interrogated without further effort in the form of corresponding data for future applications. Thereby, the permitted spatial region may be parameterized or defined, for example, for different positions, postures or movements, different instances of fitting or equipping with further instruments or devices, different reference objects, different patient types or patient positions, and/or the like, either differently or individually. This advantageously enables in many different situations and application cases in which the permitted spatial regions may differ from one another to position the reference object reliably such that the registration may be carried out successfully.

For checking the criterion, the posture of the reference object determined on the basis of the at least one camera image may be compared with the permitted spatial region or its coordinates. Thereby, an inaccuracy or uncertainty in the determination of the posture and/or the preliminary registration may be taken into account, for instance, in the form of a safety margin maintained from the edges of the permitted edge region. This safety margin may be dependent on the accuracy or uncertainty achieved in the respective individual case, so that dependent upon the individual case or situation, the permitted spatial region may be maximized or utilized as completely as possible.

The criterion proposed here, that is, the adjusting or comparison of the posture determined on the basis of the camera image with the permitted spatial region may advantageously be carried out with particularly little calculation effort and also particularly rapidly. This advantageously enables a support of a respective user during positioning of the reference object by the signal at least almost in real time.

In an advantageous development, for the checking, a specified value table or database is interrogated in which the permitted spatial region is defined, in particular, via at least one specified spacing from at least one other component of the X-ray device and/or from a midpoint of a field of view of the camera. In other words, the permitted spatial region does not have to exist, for example, as a three-dimensional simulation model. Rather, it may be stored in the value or assignment table, for example, for different postures of the reference object or for different spacings of the reference object from one or more components of the X-ray device or from the midpoint of the field of view of the camera, whether the criterion is fulfilled, that is, whether the respective position of the reference object falls within the permitted spatial region or if a successful registration is expected to be possible. Because a value or assignment table of this type may be processed or evaluated particularly easily, rapidly and with little effort, where relevant, by interpolation or a model function parameterized via the value table, in this way, the checking of the criterion and thus a corresponding support for the user or personnel during positioning of the reference object may be further simplified and accelerated.

In a further advantageous embodiment, it is checked as the criterion or as part of the criterion whether the reference object is expected to be mapped in sufficient quality and/or frequency for the registration in its current posture during recording of the X-ray images. For this purpose, the recording of the X-ray images is simulated. In other words, therefore, a virtual imaging is carried out purely computationally or computer-aided, in particular, according to or taking account of a movement or relative movement of the X-ray device planned for the respective intervention or examination. On the basis of the simulation, it may then be determined whether the criterion is fulfilled and thus the registration is at least expected to be successfully executable. Particularly advantageously, in this way, it may be determined in advance particularly exactly and reliably whether the registration is expected to be successful or will fail, wherein here also the X-ray device does not have to be switched on before the actual registration or before the actual registration attempt, that is, no X-ray images is recorded.

By the virtual simulation of the recording of the X-ray images for the registration, it may advantageously be determined and taken into account particularly reliably whether the reference object is situated not only in the recording region or in the reconstruction volume, but also whether sufficiently many or sufficiently different viewing angles are recorded or would be recorded in order to determine its posture actually or with sufficient accuracy. Thus, dependent upon the shape of the reference object, it would certainly be possible also to record a plurality of images of the reference object from different viewing angles, without the posture of the reference object being reliably determinable or reconstructable from these images. For example, in the case of a relatively flat reference object, a recording of a narrow end side of the reference object may provide significantly less position or orientation information regarding the reference object than a recording of the reference object at another angle, in particular, from a direction that is not perpendicular to any side face of the reference object.

For the simulation of the recording of the X-ray images or the mapping of the reference object resulting therefrom, a corresponding computer model or simulation model of the X-ray device and a virtual model of the reference object may be provided to a specified simulation algorithm or model as input data. Similarly, a movement, recording frequency and/or the like planned for the recording of the X-ray images may be provided as input data.

In an advantageous development, during the simulation, a respective current position of a respective patient to be imaged or a position of the patient planned for the recording of the X-ray images is taken into account in that on the basis of expected instances of covering of the reference object in the X-ray images by anatomical structures of the patient, expected inaccuracies in the recognition or posture determination of the reference object are determined. Such inaccuracies may then be used, for example, according to the safety margin described and/or compared with a specified accuracy threshold. For example, for each planned intervention or procedure, different requirements are placed on the accuracy of the registration. Thus, for instance, for spinal interventions, positional accuracies and thus also a corresponding registration accuracy of less than 1 mm may be required, while for interventions on movable and deformable soft tissues or organs such as the liver, significantly larger inaccuracies are permitted or may be permissible, for example, in the region of several millimeters.

In order to determine the instances of covering, for example, a patient model which contains X-ray visible anatomical structures and/or describes an X-ray attenuation for different regions or along different transillumination directions may be specified. This patient model may be or may have been generated, for example, on the basis of an available older CT data set of the respective individual patient or, for example, a specified standardized or average patient model.

Specifically, during a positioning of the reference object outside a center of the recording region or of the planned reconstruction volume, the accuracy of the posture determination of the reference object may be worsened in comparison with a central positioning. Instances of covering of the reference object in the X-ray images, for example, by a bone of the respective patient may then lead to a required accuracy for the posture determination and thus for the registration and finally for the later navigation no longer being maintained. Thus, the simulation of such instances of covering proposed here may particularly reliably enable or provide a successful registration with sufficient accuracy.

In a further advantageous embodiment, as the criterion or as part of the criterion, a spacing from a beam source and/or from a detector of the X-ray device which the reference object would have in its current posture during the recording of the X-ray images is evaluated. This may include a comparison of the spacing with a specified threshold value or a specified minimum and/or maximum spacing. The spacing may herein be determined automatically on the basis of the determined posture and specified properties or parameters or a specified model of the X-ray device and/or a planned movement or trajectory of the X-ray device. In other words, it may be taken into account herein not only whether the reference object is, in principle, situated sufficiently within the recording region, but an imaging geometry actually existing during the respective planned recording of the X-ray images may also be taken into account. Thus, in a 2D projection image, the reference object may appear or be mapped, for example, differently or with a different level of detail, depending upon whether it is nearer to the detector or nearer to the beam source.

Furthermore, in particular, a decentralized positioning of the reference object, a conical or pyramidal beam geometry and a restriction of a recording angle region to less than 360° may lead, depending upon the position of the beam source and the detector relative to the reference object, to the reference object being situated within or outside the beam cone, that is, being mapped or not mapped, specifically also when it is, in principle, situated within the recording region of the X-ray device. By taking account of the spacing of the reference object from the radiation source and/or the detector, that is, taking account of the imaging geometry, it may thus be provided particularly reliably in advance that the registration may be carried out successfully and with sufficient accuracy.

Herein, a plurality of criteria or conditions may also be combined with one another. For example, at a greater separation of the reference object from the beam source or from the detector, a requirement for the quality or accuracy of the mapping may increase accordingly. That is, for example, an influencing by instances of covering or a reduced information content of a respective projection image due to the imaging angle may be more critical. Therefore, if, for example, corresponding threshold values are specified, they may be adapted dynamically or dependent upon other parameters or parameter values or conditions, in particular, automatically, or different corresponding threshold values may be specified for different conditions or situations and then selected automatically.

In a further advantageous embodiment (in particular, when the criterion is initially not fulfilled) dependent upon the determined posture of the reference object, it may be specified or selected automatically on which side of the reconstruction volume the detector and the beam source of the X-ray device are each, or are each to be, positioned for recording the X-ray images in order to maximize a likelihood of the success of the registration or to fulfill the criterion at least with a specified minimum probability. For this purpose, for example, the alignment of the X-ray device, (that is, the arrangement of detector and beam source), may be specified or selected, which leads to the reference object being situated as fully as possible within the beam cone of the X-ray radiation or as centrally as possible in this beam cone or that an apparent size or a mapping scale of the reference object is sufficiently large in at least one part of the projection images. Additionally, or alternatively, the alignment of the X-ray device which leads to at least one specified threshold value, for example, for the spacing of the reference object from the beam source or from the detector for an expected or simulated imaging quality and/or a number of projection images in which the reference object is imaged, and/or other such, is undershot as far as possible or (depending upon the definition of the threshold value) exceeded, may be specified or selected.

Similarly, dependent upon the determined current posture of the reference object, the trajectory for a beam source and/or a detector of the X-ray device to be followed during recording of the X-ray images may be selected automatically, in particular, from a plurality of specified trajectories. In other words, a spatial and/or temporal path, that is, a movement for the beam source and/or the detector may be specified or adapted in the context of the adaptation described in order to maximize a probability for the success of the registration or to fulfill the criterion at least with a specified minimum probability. Herein also, the mapping of the reference object by the X-ray device is improved or optimized as described.

In an advantageous development, for specifying the alignment of the X-ray device or the trajectory for the beam source and/or the detector from a plurality of specified alignments or trajectories, the one which brings about a minimum change as compared with the respective previously provided alignment or trajectory and/or which offers the best level of fulfillment of the criterion is automatically selected. Provided, therefore, that a plurality of specified calibrated postures or trajectories of the X-ray device are specified for recording the X-ray images, from these, for example, the correspondingly most suitable may be selected in order to be able to carry out the registration as reliably as possible or with the greatest possible accuracy. For example, in a specified first alignment or trajectory, it may be provided that the detector is or remains arranged substantially above, and the beam source is or remains substantially below, the respective patient, whereas in a specified second alignment or trajectory, this is exactly reversed. Depending upon the trajectory, the detector and the beam source may thus sweep different angular ranges during the recording of the X-ray images. Both trajectories may thereby lead geometrically to the same reconstruction volume. If, however, the reference object is situated entirely or partially outside this reconstruction volume, then the angular range swept out by the beam source and the detector during the recording of the X-ray images may be decisive for the visibility of the reference object in a sufficient number of projection images with a sufficient angular difference between the respective projection vectors, because the beam cone has a smaller width closer to the beam source and thus passes through a smaller spatial volume than closer to the detector.

By the automatic selection of the alignment or the trajectory of the X-ray device proposed here, possibly without influencing the reconstruction volume and thus without impairing the planned intervention or examination, the probability of a successful registration may advantageously be increased or an effort needed for a successful registration, for instance, for repositioning the reference object, may be minimized.

In a further advantageous embodiment, on fulfillment of the criterion, the reference object is spatially fixed, that is, fastened or set relative to at least a first part of a system used for the method, in particular, the system as described below. In the event of a movement of a second part of the system during the recording of X-ray images by the X-ray device (for example, during an intervention or examination subsequent to the registration), the registration is then automatically maintained or updated in relation to the reference object or its posture.

For example, the reference object may be fastened on a holder of the beam source or the detector and the registration may then be maintained or updated during a movement of a patient table or patient support. Similarly, the reference object may be fastened, for example, on the immovably held patient table or patient support and the registration may then be maintained or updated during a movement of the camera or the navigation system. In this way, in a particularly large number of situations, a continuous navigation or navigation support may advantageously be offered particularly flexibly, in particular, without a workflow or even the respective intervention having to be interrupted therefor, for example, in order to position the reference object anew and to carry out respective new posture determinations by the X-ray device and the camera or the navigation system.

In a further advantageous embodiment, on non-fulfillment of the criterion, by the signal, an automatic, (e.g., optical or graphical), user guidance is activated, by which a respective user is notified of a possible position change of the reference object, by which the criterion may at least be expected to be fulfilled. For example, for this purpose by a laser or a projector or the like, an arrow or a line may be generated or projected and/or, for example, the permitted region, (e.g., in color), may be marked by a corresponding outline or an aerial illumination. Similarly, a corresponding representation may be output, for example, on a screen or by a pair of AR or VR goggles or an HMD or the like.

Particularly advantageously, different regions may be marked in a stepped manner, depending on which registration or navigation accuracies are to be expected on a positioning of the reference object in the respective region, wherein the accuracy may thereby relate to an anatomical navigation region relevant for the respective planned intervention or may apply to the navigation region.

Additionally or alternatively to the optical user guidance, for example, an acoustic user guidance may be possible in which, for example, by variation of a sound pitch or a temporal spacing between individual tones of a series of signal tones, an approach or distancing of the reference object in relation to the permitted spatial region and/or an expected quality or accuracy of the registration or of the later navigation may be determined.

As described, the corresponding regions or accuracies may thereby be determined or estimated on the basis of a specified or pre-calculated value table and/or by simulation, possibly dependent upon the respective planned intervention or examination, because different conditions or requirements may exist for different interventions.

By the automatic user guidance proposed here, the reference object may be reliably positioned particularly rapidly and easily without additional operational acts by the user so that a successful registration may be carried out with the respectively required accuracy, even by untrained or inexperienced users. Thus, the corresponding operational sequence may be further narrowed down and may run particularly efficiently.

A further aspect of the present disclosure is a computer program product which includes commands or control instructions which on their execution by a system, in particular, its data processing apparatus, cause this system to carry out a method in at least one embodiment. In other words, the computer program product codes or represents the method acts of the method. The computer program product may thus include a corresponding computer program which implements the method acts of the method. Similarly, the computer program product may be a computer-readable data carrier on which a corresponding computer program is stored or may include a data carrier of this type.

The method may accordingly be computer-implemented in whole or in part.

A further aspect of the present disclosure is a system which includes an X-ray device, a navigation system, a camera, and a data processing apparatus. The camera may be part of the navigation system or different or separate therefrom. The system is configured, in particular, for the automatic or semi-automatic performance of at least one embodiment of the inventive method. The system or its constituents or components may thus be, in particular, the apparatuses mentioned in association with the other aspects of the present disclosure. Accordingly, the system may have some or all of the properties, apparatuses, components and the corresponding advantages mentioned in association with one or more of the other aspects of the present disclosure.

For the performance of the method, the data processing apparatus of the system may be designed and configured for loading and carrying out the computer program product or computer program. Similarly, the data processing apparatus of the system may have a computer-readable data carrier on which a computer program is stored. For carrying out this computer program or a corresponding program code, the data processing apparatus may have a processor, (e.g., a microprocessor, microchip, or microcontroller), or a corresponding hardware circuit or the like. In addition, the data processing apparatus may have a data memory store connected to the processor and one or more interfaces for receiving or outputting data.

The system may have an optical and/or acoustic signal output apparatus for output of the signal for adaptation of the relative alignment between the X-ray device and the reference object on non-fulfillment of the criterion. The system or apparatus may include a light source, a loudspeaker, and/or a screen or the like.

The properties and developments as set out above and in the following of the method, the computer program product and the system and also the corresponding advantages are each analogously and reciprocally transferable between these aspects of the disclosure. Such developments of the aspects which have embodiments which, for the avoidance of unnecessary redundancy, are not explicitly described here in the respective combination or are not separately described for each aspect of the disclosure, thus also belong to the disclosure.

BRIEF DESCRIPTION OF THE DRAWINGS

Further features, details, and advantages of the present disclosure are disclosed in the following description of exemplary embodiments and are illustrated in the drawings, in which.

The components of the embodiment variants as described in the exemplary embodiments each represent individual features of the disclosure that are to be regarded as independent of one another and each also further develop the disclosure independently of one another and are thus also to be considered individually, or in a different combination from that shown, as a constituent of the disclosure. Furthermore, the embodiment variants described are also enhanceable with others of the previously described features of the disclosure.

DETAILED DESCRIPTION

Figure 1:
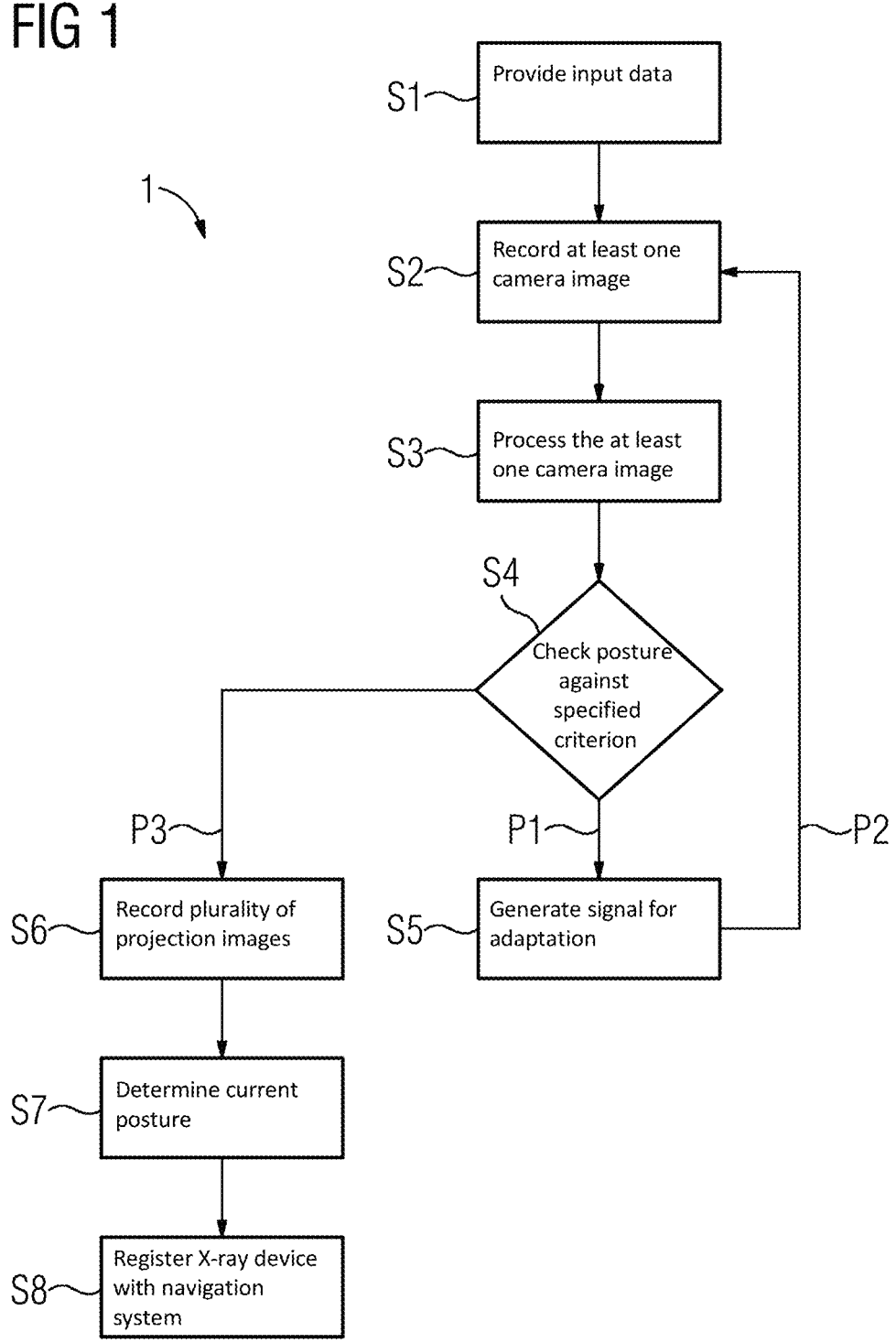
FIG. 1 depicts an exemplary schematic flow diagram for a method for registering an X-ray device with a navigation system.
Figure 2:
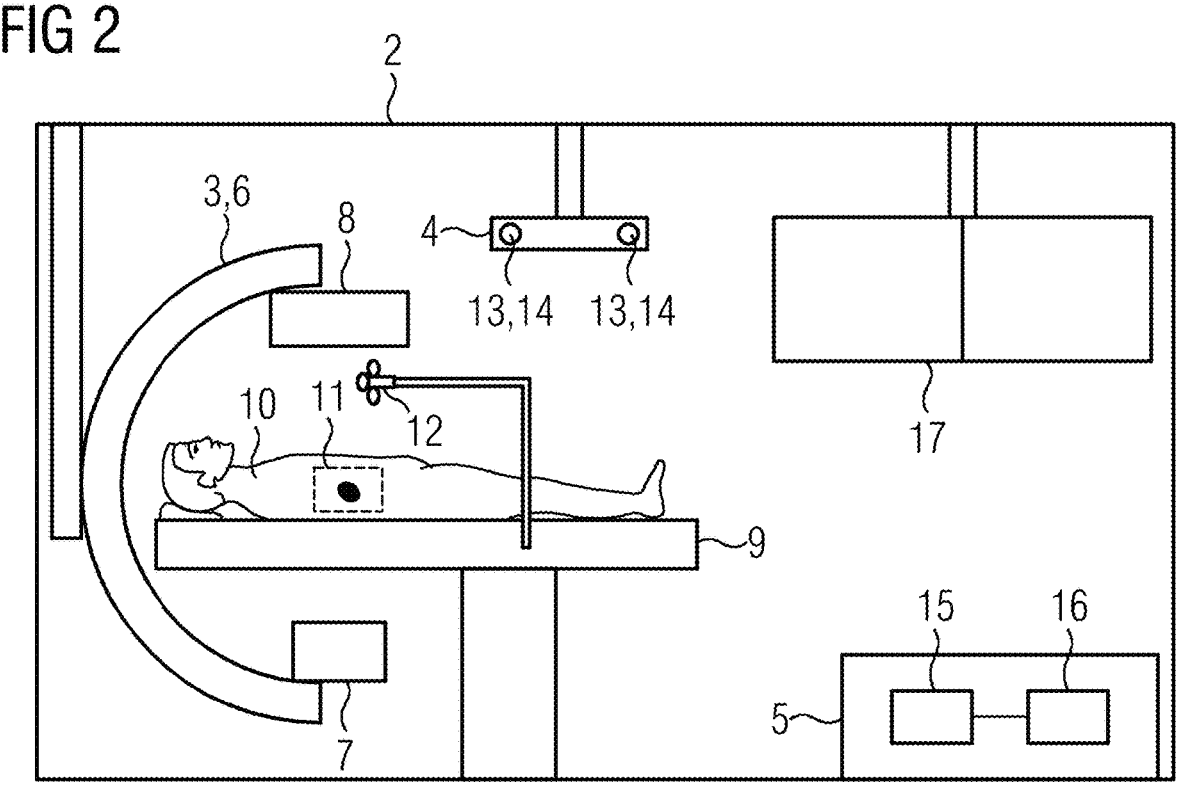
FIG. 2 depicts a schematic representation of an example of a system for carrying out the method.

FIG. 1 shows schematically an example of a possible flow diagram 1 for a method for registering two devices with one another in the context of technology-supported or computer-supported medicine. In concrete terms, the method may be used for a system 2 represented in FIG. 2. The system 2 herein includes an X-ray device 3 and a navigation system 4 which are to be registered with one another. The system 2 further includes a data processing apparatus 5, for example, a computer connected to the X-ray device 3 and the navigation system 4.

The X-ray device 3 is configured here, for example, as a C-arm device and accordingly has a C-arm 6 on which a beam source 7 and a detector 8 arranged opposite thereto are held. The X-ray device 3 herein further includes a patient table 9 on which a patient 10 to be imaged or examined lies. By corresponding movement of the C-arm 6, the beam source 7 and the detector 8 may be moved along the patient 10 arranged therebetween or may be rotated around the patient 10 and the patient table 9. Thereby, by the X-ray device 3, therefore, X-ray recordings of at least a part of the patient 10 may be made from different angulations or viewing angles. In particular, by the X-ray device 3, a reconstruction volume 11 which may include, for example, an anatomical or medical region of interest of the patient 10 may be irradiated or mapped from different viewing angles, so that a three-dimensional reconstruction of the reconstruction volume 11 may be created from corresponding 2D projection images.

In a recording region that may be captured by the X-ray device 3, but which is at least partially arranged outside the reconstruction volume 11, an X-ray visible reference object 12 is arranged here. As described below, by the reference object 12, the desired registration of the X-ray device 3 and of the navigation system 4 with one another or to one another may be carried out.

For the registration and prior providing that the registration may be carried out successfully, the reference object 12 is also situated in a field of view or recording region of the navigation system 4. The navigation system 4 herein has a plurality of apparatuses. These are, in particular, a camera 13 for capturing or mapping the reference object 12. The latter is situated in a corresponding field of view or recording region of the camera 13. This may also be the case if the camera 13 is not part of the navigation system, but is, for example, an additional ceiling camera or the like.

In the present example, the camera 13 may be configured, in particular, as a stereo camera for recording stereoscopic or 3D camera images.

A further apparatus of the navigation system herein is a signal output apparatus 14, by which an optical and/or acoustic signal may be output, for example, in order to inform or instruct corresponding personnel or a respective user of the system 2. The signal output apparatus 14 or a corresponding apparatus may also be provided separately from the navigation system 4.

Data provided by the X-ray device 3 and the navigation system 4 may be processed by the data processing apparatus 5. For this purpose, the data processing apparatus 5 has, as schematically indicated here, at least one processor 15 and a computer-readable data store 16 connected thereto. In the present example, a computer program or program code is stored on the data store 16, whereby the method for registering the X-ray device 3 and the navigation system 4 with one another is implemented, for example, according to the flow diagram 1. Accordingly, some or all method acts S1 to S8 and/or program paths P1 to P3 of the flow diagram 1 or of the corresponding method may represent relevant program modules, commands, control instructions, methods, or functions of the computer program or program code. The computer program stored on the data store 16 is then executable by the processor 15 to carry out the method.

Furthermore, the system 2 herein includes a screen 17, by which, for example, images and/or data generated by the X-ray device 3, the navigation system 4 and/or the data processing apparatus 5 may be output.

Herein, therefore, the registering of the X-ray device 3 or of its coordinate system with the (e.g., optical) navigation system 4 or its coordinate system may be achieved via the reference object 12. As in the present example, the reference object 12 may be situated entirely or partially outside the reconstruction volume 11 of the X-ray device 3, so that accordingly, it will be visible only in part of the planned 2D projection images. In principle, from a plurality of such 2D projection images which have been recorded from different angles, for example, by an angular region or an angulation region of at least 30°, a 6-degrees of freedom (DOF) posture, that is, a three-dimensional position and orientation of an object of specified, that is, known, shape—herein the reference object 12—may be reconstructed. It is thereby problematic that it may be estimated only with great difficulty and unreliably whether the reference object 12 will be mapped in its respective posture in sufficient projection images and over an angular range sufficient for the determination or estimation of the posture. An asymmetrical shape of the reference object 12 may lead as a complication, to the posture, depending upon the orientation of the reference object 12 or depending thereon in which projection images the reference object 12 is mapped, being able to be detected or determined with different levels of success. This problem may be countered by the method according to the flow diagram 1, which is described below making reference to FIG. 2.

In the method act S1, input data may be provided to the data processing apparatus 5. This input data may include the planned procedure or the examination of the patient 10 including an imaging to be carried out therein by the X-ray device 3 or may describe corresponding movements or trajectories of the X-ray device 3, but also properties, restrictions, mapping parameters and/or a model of the X-ray device 3, a virtual model of the reference object 12, a patient model of the patient 10, a computer model for the simulation of the imaging and corresponding mapping properties or mapping results, a criterion for evaluating the posture of the reference object 12 in relation to the desired registration or its likelihood of success or its accuracy, for example, corresponding definitions of a permitted spatial region, threshold values and/or the like. At least some of this data may be retrieved, where relevant, automatically by the data processing apparatus 5, for example, by the X-ray device 3 or a planning computer (not shown here), a prepared database or the like.

In the method act S2, by the camera 13, at least one camera image of the reference object 12 in its current posture is recorded.

In the method act S3, the at least one camera image is processed by the data processing apparatus 5 and, on the basis of the camera image, the current posture of the reference object 12 is thereby determined, at least in the coordinate system of the camera 13 or the navigation system 4.

In the method act S4, the posture of the reference object 12 thus determined is tested or checked against the specified criterion in order to be able to predict whether the desired registration of the X-ray device 3 with the navigation system 4 given the current posture of the reference object 12 is expected to be successful or to fail.

If, in the method act S4, the result is produced that the criterion is not fulfilled, that is the registration with the current posture of the reference object 12 is expected to fail or cannot be carried out with the desired accuracy, the method follows the program path P1 to the method act S5.

In the method act S5, a signal for adaptation of the posture of the reference object 12 or of a relative alignment between the X-ray device 3 and the reference object 12 is generated by the data processing apparatus 5 and is output by the signal output apparatus 14. In other words, a message is hereby issued to the respective user as to whether the reference object 12 is suitably positioned for the posture determination and registration. In addition, a user guidance, that is, a navigated orientation support for the user may take place in order to support the user in the reorientation or repositioning of the reference object 12, so that in a new posture of the reference object 12, it is expected that the registration may be carried out successfully. Thereby, errors, inaccuracies, or uncertainties may be taken into account in the posture determination carried out on the basis of the at least one camera image.

In the user guidance or the repositioning or reorientation of the reference object 12, this may be tracked, for example, continuously by the camera 13 and the criterion may be continually checked. Similarly, at least one camera image of the reference object 12 in its then new posture may be recorded regularly or, for example, anew on a corresponding operating input by the user, this posture may be determined anew on the basis of the respective camera image and the criterion for this new posture may be evaluated anew. The method acts S2 to S5 may thus be run through iteratively, as is indicated here by the program path P2.

Thereby, the expected success of the registration, similarly to its accuracy or an expected navigation accuracy (resulting, for example, within the reconstruction volume 11) may be determined or estimated and output. This may take place, for example, on the basis of specified or pre-calculated value tables or on the basis of a corresponding simulation.

On passing through the method acts S2 to S5, by the camera 13, not only the reference object 12, but for example, also the X-ray device 3 may be at least partially captured and, on the basis of the at least one camera image, a coarse or preliminary registration of the position of the X-ray device 3, for example, of the C-arm 6 and/or of the patient table 9 with the navigation system 4 or its coordinate system may then also be carried out. The posture of the reference object 12 determined on the basis of the at least one camera image may then already be determined, for example, in a common coordinate system for the X-ray device 3 and the navigation system 4. As described, pre-existing knowledge or data, knowledge regarding the course of the planned CT trajectory or the projection geometry, for example, relative to the C-arm 6 or relative to the patient table 9, may be transferred via a corresponding interface to the data processing apparatus 5 or retrieved or loaded thereby. Previously calculated, specified permitted spatial regions or value ranges for the posture of the reference object 12, for example, relative to the C-arm trajectory or the projection geometry, may be loaded and taken into account. In addition or alternatively, a simulation of the planned X-ray imaging or the position recognition based thereon for the reference object 12 on the basis of its current posture and inaccuracies thereby likely to occur or expected may be carried out.

Thereby, a current or planned position of the patient 10 and a patient model based thereon may be taken into account in advance, in order to take account in the simulation of instances of covering of the reference object 12, for example, by X-ray visible anatomical structures of the patient 10, that is, before the recording of the actual real X-ray images, so that uncertainties or inaccuracies arising therefrom in the recognition of the reference object 12 or the determination of its posture on the basis of the X-ray images may be anticipated in advance and may be taken into account during evaluation or checking of the criterion.

On evaluation or checking of the criterion, that is, ultimately for the statement of whether the current posture of the reference object 12 is permitted for the registration in the respective application case, a spacing of the reference object 12 from a later anatomical navigation region, for example, the reconstruction volume 11 or a subregion of the reconstruction volume 11 may be taken into account. It may thereby be the case, for example, that the requirements or threshold values for the accuracy of the determination of the posture or the registration are greater the further the reference object 12 is removed from the anatomical navigation region.

Similarly, a best calibrated trajectory or rotation of the X-ray device 3 or of the C-arm 6 may be selected automatically from specified calibrated trajectories or rotations, for example, in the context of the user guidance in the method act S5 or independently thereof, in order to optimize the probability of success and/or accuracy of the posture determination or the registration. For example, the alignment of the C-arm 6 shown in FIG. 2 may be selected in which the detector 8 is positioned above the patient table 9 and thus closer than the beam source 7 to the reference object 12 in its current posture. By this, for example, in contrast to the reverse alignment, the reference object 12 being situated outside a beam cone emerging from the beam source 7 may be prevented. The alignment of the C-arm 6 shown here may be or represent, in particular, medium, or average alignment or center of gravity alignment of the C-arm 6, resulting from a selected trajectory. The C-arm 6 may thus move about the alignment or position shown here when moving along or carrying out the trajectory. For example, when recording the X-ray images, the beam source 7 and the detector 8 may vary their position about a rotation axis of the C-arm 6 extending in the drawing plane in the longitudinal direction of the patient 10—depending on the selected trajectory, for example, by up to 90° in each direction.

If, in the method act S4, possibly after one or more iterative passes, it is determined that the criterion that with the respective current posture of the reference object 12, it is expected that the registration may be carried out with the desired accuracy is fulfilled, then the method follows the program path P3. In this case, also, a corresponding signal may naturally be output in order to indicate the correct or successful positioning of the reference object 12.

In the method act S6, a plurality of projection images, that is, X-ray images is recorded, wherein the reference object 12 is mapped in at least some of these projection images.

In the method act S7, on the basis of these projection images, the current posture of the reference object 12 is determined.

In the method act S8, the registration of the X-ray device 3 with the navigation system 4 is carried out using the determined postures of the reference object 12 as a datum or reference point. For example, an identity, that is, an agreement of the posture determined from the at least one camera image with the posture determined from the X-ray projection images or the corresponding coordinates may be assumed, postulated, or (for example, by corresponding displacements and/or rotations) created thereby.

With the registration successfully carried out in this way, the respective planned procedure for treating or examining the patient 10 may be carried out with navigation support. In particular, if the reference object 12 is fixed, as in the present example, in the posture used for the registration, on a movement of a part or a component of the system 2, the registration may be automatically maintained or updated.

By the method and the system 2 described, a predictable registration, or a prediction of a success of the registration of the X-ray device 3, (e.g., a DynaCT device), to the navigation system 4 may advantageously be enabled. A respective user may be supported in the correct positioning of the reference object 12 for the registration, and so the corresponding operational process may be made simpler and improved in its reliability. By this, advantageously, the acceptance of a navigation support in conjunction with the X-ray imaging may possibly be improved. Overall, the examples described show how by supported alignment of the reference object 12, a particularly reliable and robust registration of the X-ray device 3 with the navigation system 4 may be achieved.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for registering a set of X-ray images recorded by an X-ray device with a navigation system, the method comprising:
   recording, by a camera, an image of a specified X-ray visible reference object arranged in a recording region of the X-ray device;
   determining a current posture of the reference object based on the image;
   checking whether the determined current posture of the reference object fulfills a specified criterion, which also on an arrangement of the reference object at least partially outside a respective planned reconstruction volume of the X-ray device, predicts an expected successful registration;
   automatically outputting, on non-fulfillment of the criterion, a signal for adapting a relative alignment between the X-ray device and the reference object and/or for adapting a specified trajectory of the X-ray device provided for later recording of the X-ray images of the reference object, in order to fulfill the criterion; and
   on fulfillment of the criterion for the current posture, the adapted relative alignment, the adapted specified trajectory, or a combination thereof:
      recording the X-ray images of the reference object by the X-ray device;
      determining the posture of the reference object based on the X-ray images; and
      carrying out the registration using the determined posture as a reference.

2. The method of claim 1, wherein the criterion is defined as whether the reference object is situated in a specified permitted spatial region.

3. The method of claim 2, wherein, for the checking, a specified value table is interrogated in which the permitted spatial region is defined via at least one specified spacing from at least one other component of the X-ray device and/or from a midpoint of a field of view of the camera.

4. The method of claim 1, wherein the criterion is defined as whether the reference object in the current posture during recording of the X-ray images is expected to be mapped in sufficient quality and/or frequency for the registration, and
   wherein, for this purpose, the recording of the X-ray images is simulated.

5. The method of claim 4, wherein, during the simulation, a respective current position of a respective patient to be imaged or a position of the patient planned for the recording of the X-ray images is taken into account in that based on instances of covering of the reference object caused in the X-ray images by anatomical structures of the patient, expected inaccuracies in a recognition or posture determination of the reference object are determined.

6. The method of claim 1, wherein, as the criterion, a spacing from a beam source and/or from a detector of the X-ray device which the reference object would have in the current posture during the recording of the X-ray images is evaluated.

7. The method of claim 1, wherein, dependent upon the determined current posture of the reference object, an alignment of the X-ray device is automatically specified, stating on which side of the reconstruction volume a detector and a beam source of the X-ray device are each positioned during the recording of the X-ray images, in order to maximize a probability for a success of the registration.

8. The method of claim 7, wherein, dependent upon the determined current posture of the reference object, the trajectory to be followed by a beam source and/or a detector of the X-ray device during the recording of the X-ray images is automatically specified.

9. The method of claim 8, wherein, for the specifying of the alignment of the X-ray device or the trajectory for the beam source and/or the detector from a plurality of defined alignments or trajectories, the one which brings about a minimum change as compared with the respective previously provided alignment or trajectory and/or which offers a best level of fulfillment of the criterion is automatically selected.

10. The method of claim 1, wherein, dependent upon the determined current posture of the reference object, the trajectory to be followed by a beam source and/or a detector of the X-ray device during the recording of the X-ray images is automatically specified.

11. The method of claim 1, wherein on the fulfillment of the criterion, the reference object is spatially fixed relative to at least one first part of a system, and
   wherein, on a movement of a second part of the system during the recording of X-ray images by the X-ray device, the registration is automatically maintained or updated making reference to the reference object.

12. The method of claim 1, wherein on the non-fulfillment of the criterion, an automatic user guidance is activated by the signal, by which a respective user is notified of a possible position change of the reference object, by which the criterion is expected to be fulfilled.

13. The method of claim 12, wherein the automatic user guidance is an optical user guidance.

14. A computer program product comprising commands which, during their execution by a data processing apparatus of a system, cause this system to:

record, by a camera of the system, an image of a specified X-ray visible reference object arranged in a recording region of an X-ray device of the system;

determine a current posture of the reference object based on the image;

check whether the determined current posture of the reference object fulfills a specified criterion, which also on an arrangement of the reference object at least partially outside a respective planned reconstruction volume of the X-ray device, predicts an expected successful registration;

automatically output, on non-fulfillment of the criterion, a signal for adapting a relative alignment between the X-ray device and the reference object and/or for adapting a specified trajectory of the X-ray device provided for later recording of the X-ray images of the reference object, in order to fulfill the criterion; and on fulfillment of the criterion for the current posture, the adapted relative alignment, the adapted specified trajectory, or a combination thereof:

record the X-ray images of the reference object by the X-ray device;

determine the posture of the reference object based on the X-ray images; and carry out the registration using the determined posture as a reference.

15. A system comprising:

an X-ray device;

a navigation system;

a camera configured to record an image of a specified X-ray visible reference object arranged in a recording region of an X-ray device; and a data processing apparatus configured to:

determine a current posture of the reference object based on the image;

check whether the determined current posture of the reference object fulfills a specified criterion, which also on an arrangement of the reference object at least partially outside a respective planned reconstruction volume of the X-ray device, predicts an expected successful registration;

automatically output, on non-fulfillment of the criterion, a signal for adapting a relative alignment between the X-ray device and the reference object and/or for adapting a specified trajectory of the X-ray device provided for later recording of the X-ray images of the reference object, in order to fulfill the criterion; and on fulfillment of the criterion for the current posture, the adapted relative alignment, the adapted specified trajectory, or a combination thereof:

record the X-ray images of the reference object by the X-ray device;

determine the posture of the reference object based on the X-ray images; and carry out the registration using the determined posture as a reference.

\* \* \* \* \*